(12) United States Patent
Hentze et al.

(10) Patent No.: US 6,635,440 B1
(45) Date of Patent: Oct. 21, 2003

(54) METHOD OF ISOLATION OF RNA-BINDING COMPOUNDS

(75) Inventors: Matthias W. Hentze, Heidelberg (DE); Efrosyni Paraskeva, Larissa (GR)

(73) Assignee: European Molecular Biology Laboratory, Heidelberg (DE)

( * ) Notice: Subject to any disclaimer, the term of this patent is extended or adjusted under 35 U.S.C. 154(b) by 0 days.

(21) Appl. No.: 09/600,962

(22) PCT Filed: Jan. 26, 1999

(86) PCT No.: PCT/IB99/00218

§ 371 (c)(1),
(2), (4) Date: Oct. 23, 2000

(87) PCT Pub. No.: WO99/37807

PCT Pub. Date: Jul. 29, 1999

(30) Foreign Application Priority Data

Jan. 26, 1998 (GB) ................................................ 9801631

(51) Int. Cl.⁷ ............................ C12Q 1/68; G01N 33/50
(52) U.S. Cl. ................................. 435/29; 435/4; 435/6; 435/7.1
(58) Field of Search ........................... 435/4, 6, 7.1, 29

(56) References Cited

U.S. PATENT DOCUMENTS 5,610,015 A * 3/1997 Wickens et al.
5,989,814 A * 11/1999 Frankel et al.

OTHER PUBLICATIONS

Paraskeva et al (1998) Proc. Natl. Acad. Sci. USA 95:951–956.*
Helm et al (1995) Nature 373:663–664.*

* cited by examiner

Primary Examiner—Remy Yucel
Assistant Examiner—Bronwen M. Loeb
(74) Attorney, Agent, or Firm—David G. Conlin; Dianne M. Rees; Edwards & Angell, LLP

(57) ABSTRACT

The present invention provides a method of isolation of compounds that bind specifically to RNA or that alter the affinity of known compounds for RNA. The method utilizes changes in the levels of a fluorescent marker protein expressed in the same cell as a putative RNA-binding compound to detect those compounds of interest.

11 Claims, 10 Drawing Sheets

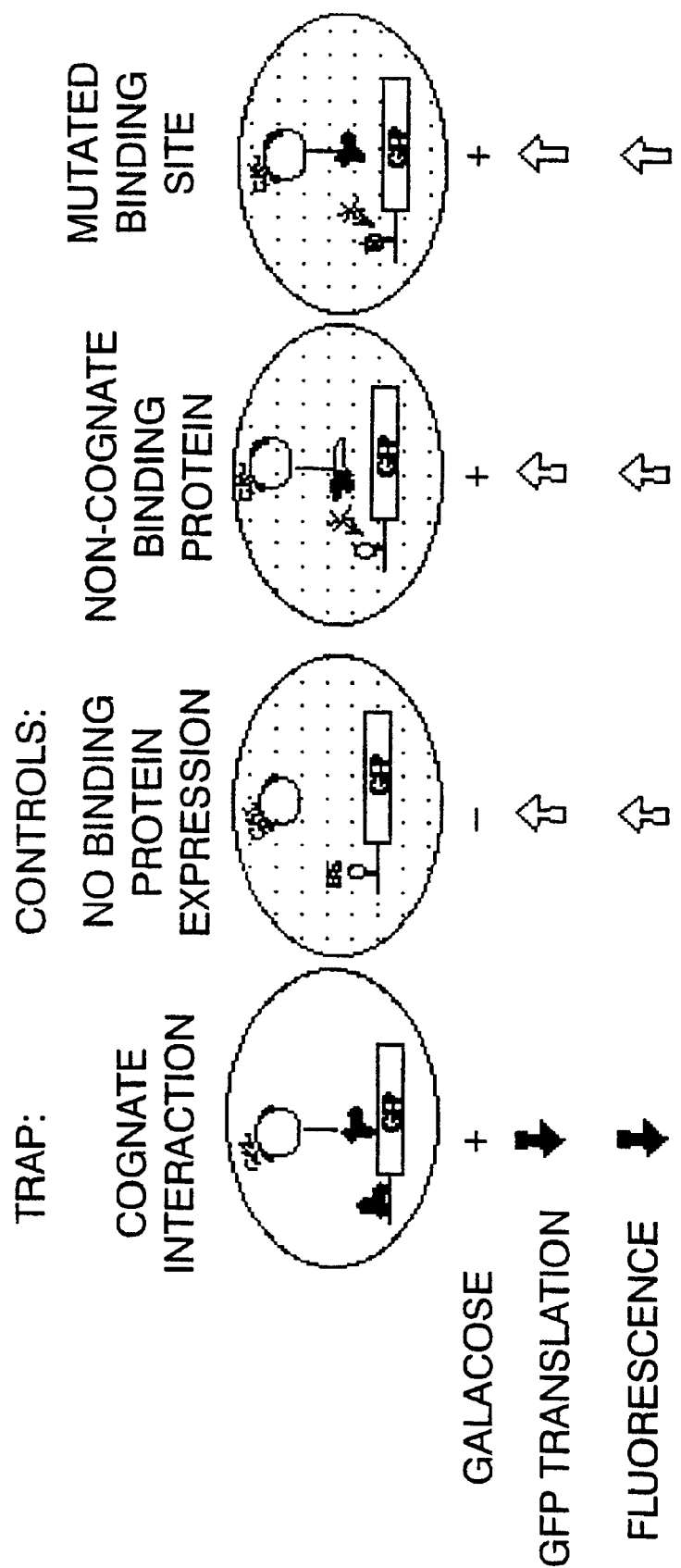

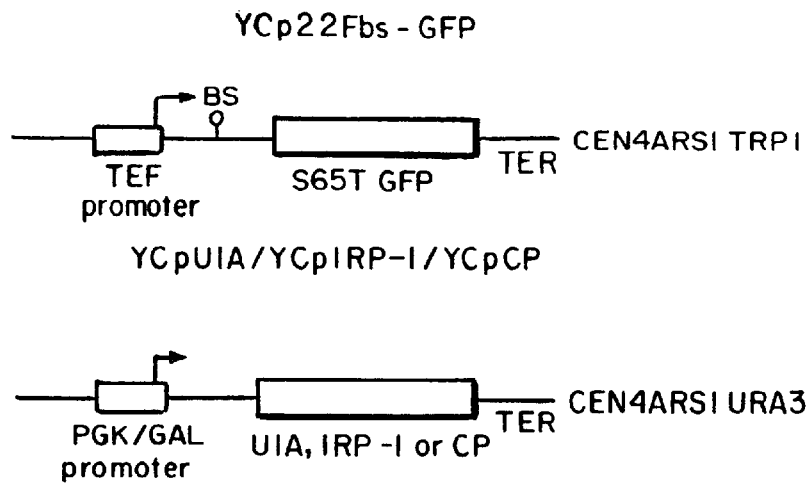

FIG. 2

```
IKEwt    aattatctaCTTAAGCTTCAACAGTGCTTGAACTTAAGaacacaaaactcgagaacatattttaatattatg
IKEmt    aattatctaCTTAAGCTTCAAAGTGCTTGAACTTAAGaacacaaaactcgagaacatattttaatattatg
U1Awt    aattatctaCTTAAGCGATTGCACTCCCGCTTAAGaacacaaaactcgagaacatattttaatattatg
U1Amt    aattatctaCTTAAGCGATTCATCTCCCGCTTAAGaacacaaaactcgagaacatattttaatattatg
MSC      aattatctaCTTAAGGACCATCAGGCCTTAAGaacacaaaactcgagaacatattttaatattatg
MSA      aattatctaCTTAAGGACCATAAGGCCTTAAGaacacaaaactcgagaacatattttaatattatg
MSAdel   aattatctaCTTAAGGACCATAAGCCTTAAGaacacaaaactcgagaacatattttaatattatg
```

FIG. 3

CONTROL = NON COGNATE BP

COGNATE INTERACTION

METHOD OF ISOLATION OF RNA-BINDING COMPOUNDS

The present invention provides a method of isolation of compounds that bind to ribonucleic acid (RNA). In particular, this method is suitable for use in identifying compounds for which a cognate RNA binding site is known. This method allows the isolation of new compounds that bind specifically to RNA and may thus be used in the study of the interactions that are important for the normal function of the cell or for the activity of viruses. This method may also be used to identify RNA binding compounds with potential efficacy as pharmaceuticals.

Proteins have important roles in the structure and function of all types of RNA (mRNA, rRNA, tRNA and viral RNA), ranging from packaging nucleic acid molecules in a stable structural configuration to mediating all aspects of RNA metabolism. Many interactions between RNA and proteins are specific for consensus recognition sites defined by the nucleic acid sequence of the mRNA. It is these interactions in particular that often have profound effects on the relative stabilities of certain RNA species, or that affect the rate and degree of translation from these mRNAs and their locations within a cell.

A rapidly increasing number of examples provide evidence that gene expression can be regulated in the cytoplasm of eukaryotic cells at the level of mRNA stability, translation, or the subcellular localisation of mRNAs (reviewed by Sachs 1993; Merrick 1992). The biological processes controlled by such mechanisms range from biological processes as diverse as early embryonic development, sexual differentiation, intelligence and viral replication. Common to these post-transcriptional methods of control is the role played by specific interactions between cis-acting sequences in the mature mRNAs and regulatory binding proteins. Most commonly, the regulatory sequences are contained within the untranslated regions at the 5' and 3' ends of the mRNA transcripts.

In prokaryotes, numerous examples of post-transcriptional regulation by repressor proteins exist. In most cases, the repressor proteins directly or indirectly occlude the Shine-Dalgarno sequence and/or the initiation codon.

In eukaryotes, one of the best examples of specific interactions between RNA and binding proteins that has been elucidated to date is the regulation of ferritin and erythroid 5-aminolevulinate synthase mRNAs by iron regulatory proteins (IRPs). IRP1 or IRP2 bind to the iron responsive element (IRE) in the 5' untranslated region of a mRNA in a position proximal to the CAP binding site and controls the initiation step of translation. It is a mutation in an IRE in the ferritin L-chain mRNA that leads to hyperferritinaemia/cataract syndrome in human patients (Beaumont et al, 1995).

More recently, further examples have been identified in eukaryotic cells, such as the L32 yeast ribosomal protein (Dabeva and Warner, 1993) and proteins acting on Drosophila spermatogenesis that are further candidates for repressors that are functionally similar to IRP. Examples have also been found that bind further downstream from the CAP structure, such as thymidylate kinase (Chu et al., 1993). LOX-BP binds to the 3' region of 15-lipoxygenase mRNA and represses its translation (Ostareck-Lederer et al, 1994).

The biological importance of RNA binding protein-binding site effector pairs means that a useful mechanism is needed by which these RNA binding proteins can be identified and further examined. Such a strategy had not proven easy to devise, partly because, in many cases, RNA-binding proteins exert their functions in cells or tissues that are not readily amenable to biochemical analysis, such as specific areas of the brain or in the germ line. The unavailability of biochemical material imposes cumbersome limitations on the identification and cloning of biologically important RNA-binding proteins operating in such systems, particularly when compounded by a lack of possible genetic approaches.

To circumvent such limitations, alternative strategies to identify and study RNA-protein interactions have been devised, based on phage display (Laird-Offringa et al., 1995), transcription termination (Harada et al., 1996) or translation in $E.$ $coli$, (Jain and Belasco, 1996) or on transcription initiation in yeast (SenGupta et al., 1996; Putz et al, 1996).

One approach to study RNA-protein interactions has previously been developed by the present inventors. This approach is based on the realisation that the binding of protein to specific sites near the 5' end of an mRNA molecule causes its translation to be repressed both in mammalian cells and in yeast (Stripecke and Hentze, 1992; Stripecke et al., 1994; Gray and Hentze, 1994). RNA binding proteins with physiological functions unrelated to eukaryotic mRNA translation were found to function as translational repressor proteins when their specific cognate binding site was introduced into the 5'UTR in a position similar to that of the IRE in ferritin mRNA (Stripecke et al., 1994).

Due to the step-wise nature of the translational initiation process, in which ribosome subunits and cofactors must have access to its their binding sites on the mRNA molecule, translational repression using the Stripecke method appears not to be restricted by the normal physiological function of the RNA-binding protein used. The Stripecke method thus allows the study of almost any protein-RNA binding site pair.

In the Stripecke method, the cognate binding sites for the bacteriophage protein MS2-CP and the spliceosomal component U1A were each cloned into the 5'UTR of luciferase indicator mRNAs using a restriction enzyme site nine nucleotides downstream of the major transcription initiation site. The repressor proteins were cloned under an inducible GAL4/PGK promoter so that luciferase activity could be assayed in the presence and absence of binding protein. It was found that in the presence of both the cognate binding protein and the RNA binding site in the luciferase mRNA, luciferase activity decreased in correlation with the affinity between the binding protein and the binding site in the mRNA. This correlation was also shown to exist in HeLa cells. The translation of the luciferase indicator constructs could be decreased up to ten-fold by this mechanism of repression.

This system thus allows the study of the affinities between specific RNA binding sites and cognate positions. However, in order to be able to assay for luciferase activity the cells need to be harvested and lysed. This means that no linkage between phenotype (i.e. repression of translation caused by the presence of an efficacious binding protein) and genotype (the gene which coded for the active binding protein) is retained. This method is therefore only suited to the assessment of the degree of affinity with which a specific binding pair interact and essentially does not allow the isolation of novel RNA binding proteins or their coding genes.

There is thus a great need for a method of detection of nucleic acids that code for RNA binding compounds, particularly proteins.

SUMMARY OF THE INVENTION

According to the present invention there is provided a method for the isolation of nucleic acid coding for a RNA-binding compound, said method comprising the steps of:
a) expressing in a host cell
  i) one or more candidate nucleic acids to be screened for coding for the RNA binding compound, and
  ii) a nucleic acid comprising a coding region for a fluorescent marker protein, wherein the nucleic acid comprising the coding region for the fluorescent marker protein includes a binding site for the RNA-binding compound,
b) selecting a host cell that exhibits an altered level of fluorescence from levels found in a host cell containing ii) alone; and
c) isolating the nucleic acid coding for the RNA binding compound from the selected cell.

This approach is referred to as TRAP (Translational Repression Assay Procedure) and makes use of the discovery that the binding of a compound to a sequence that is present in a mRNA species prevents its translation. The mechanism of this prevention is thought to be by steric hindrance, that either precludes the binding of the ribosome at its binding site in the mRNA species or that prevents its passage along the mRNA molecule. This leads to a decrease in the amount of protein that is translated from the mRNA species.

In the method of the present invention, a binding site is introduced into the transcribed portion of a nucleic acid that codes for a selectable fluorescent marker. Preferably, the binding site is introduced into the Cap-proximal region of the 5'UTR of the transcribed mRNA. This altered nucleic acid is then introduced into a host cell, such as yeast.

A population of transformed host cells is co-transformed with a number of candidate nucleic acids for RNA binding compounds, such as, for example, are contained within a cDNA library. The candidate nucleic acids may code for proteins or for other nucleic acid molecules with RNA binding activity, such as ribozymes. In a preferred embodiment of the invention, the candidate nucleic acids are cloned under the control of an inducible promoter in order that expression of the encoded compound may be tightly controlled.

The candidate nucleic acid and the nucleic acid coding for the fluorescent marker may be introduced into the host cells as part of plasmids, or they may be integrated into the chromosome of the host cell.

The cells are then cultured in an environment that allows translation to occur. Co-transformants that carry a cDNA molecule encoding a compound that alters translation of the selectable fluorescent marker can then be identified. The binding of the compound to the mRNA prevents access of the translation machinery and so alters the degree of translation of the marker mRNA relative to cells which do not contain a compound that interacts with the RNA binding site. Some cells then exhibit altered levels of fluorescence relative to the level of fluorescence displayed by cells that only contain the nucleic acid that comprises the RNA binding site and encodes the fluorescent marker. These cells will possess altered levels of the fluorescent marker protein and therefore are likely to contain a candidate nucleic acid encoding a compound that binds to the RNA binding site of interest.

The method of the present invention is ideally suited to the selection of cells in which translation has been repressed. In this instance, cells will be selected that exhibit reduced levels of fluorescence to the mean fluorescence level.

It has been found that in order to identify RNA binding compounds of interest using this method, it is preferable to subject the cell population to multiple cycles of enrichment, each time selecting for cells that exhibit altered levels of fluorescence. Ideally, at least three cycles are performed.

This strategy allows the identification and cloning of nucleic acids encoding compounds, particularly proteins, that exist in very low abundance in vivo or for which there is a lack of suitable biological material to allow separation of the compound in sufficient amounts for cloning of the encoding gene. This method also allows the selection of nucleic acids encoding molecules other than proteins that possess an affinity for a particular RNA sequence motif. Such molecules include small bioactive peptides and catalytic RNA molecules such as ribozymes.

The method of the present invention allows the selection of a candidate nucleic acid that encodes an RNA binding compound. The RNA binding compound selected using the method of the present invention may have any number of physiological functions, such as recognition of a response element in an RNA sequence (such as in the case of the IRE), possession of ribonuclease activity, participation in the process of RNA splicing, contribution to the stability of an RNA molecule, tRNA synthetase activity or any other function or activity that derives from a specific interaction with an RNA sequence.

As used herein, the term "RNA binding compound" is taken to mean any compound that interacts specifically with a known RNA binding site. By specific interaction is meant that the affinity constant for the interaction between binding protein and RNA sequence is lower than 10 $\mu$M. Preferably, the affinity constant is lower than 1 $\mu$M. By "RNA binding site" is meant any motif that is present in the sequence of an RNA molecule. The sequence motif may comprise any number of nucleotides, although consensus sequence motifs for RNA binding proteins normally comprise between 5 and 40 nucleotides.

The RNA binding compound may comprise any compound or combination of compounds that can be encoded by DNA or RNA molecule, and may therefore comprise nucleic acid such as RNA or a ribozyme, or may comprise a peptide or polypeptide. Preferably, the RNA binding compound comprises a peptide or polypeptide.

If proteinaceous, the compound need not be an entire protein or protein module, but may instead be any peptide fragment or polypeptide component of a protein that possesses RNA binding activity. The compound may bind to RNA as a single entity or may dimerise to form homodimers or heterodimers that are then able to bind to a specific RNA sequence. In this instance, the complementary protein that is necessary for the binding activity must also be present in the cell.

Additionally, the peptide or polypeptide identified may not itself possess RNA binding activity, but may instead be necessary for the RNA binding activity of another compound that is present in the cell. For example, the identified peptide or polypeptide may form a heterodimer whose integrity is essential for the correct recognition of an RNA sequence motif.

According to a second embodiment of the present invention there is provided a method for the isolation of nucleic acid coding for a compound that alters the affinity of interaction between a RNA-binding site and a RNA binding compound, said method comprising the steps of:
a) expressing in a host cell
  i) one or more candidate nucleic acids to be screened for coding for the compound that alters the affinity of interaction between the RNA-binding site and the RNA binding compound, ii) a nucleic acid comprising a coding region for the RNA binding compound, iii) a nucleic acid comprising a coding region for a fluorescent marker protein, wherein the nucleic acid comprising the coding region for the fluorescent marker protein includes a binding site for the RNA-binding compound, b) selecting a host cell that exhibits an altered level of fluorescence from levels of fluorescence found in a host cell containing ii) and iii) alone; and c) isolating from the selected cell the nucleic acid coding for the compound that alters the affinity of interaction between the RNA-binding site and the RNA binding compound.

The method of the present invention may also be used to identify compounds that alter the affinity of interaction between a known RNA binding compound and its binding site. For example, a cell population may be transformed with both a nucleic acid that comprises a binding site for a RNA binding compound and that encodes a fluorescent marker protein and an additional nucleic acid that encodes a RNA binding compound. This cell population may then be transformed with nucleic acids that encode, or incubated in the presence of agents that are candidates for altering the affinity of interaction between the RNA binding site and its cognate binding protein. Such agents may be pharmaceutical drugs or small molecules such as bioactive peptides. Cells that contain agents that effectively alter the affinity of interaction between RNA binding compound and binding site will exhibit altered levels of fluorescence relative to levels in cells that only contain a nucleic acid comprising the binding site for the RNA binding compound and that encodes the fluorescent marker protein and the nucleic acid that encodes the RNA binding compound.

As used herein, by "candidate nucleic acid" is meant a nucleic acid that codes for a single nucleic acid or protein species. Accordingly, the candidate nucleic acid may be any fragment of a gene that encodes a compound with specific RNA binding activity or whose presence is required for the RNA binding activity. The candidate nucleic acid may be a naturally-occurring nucleic acid, or it may be partially or wholly synthetic. For example, the nucleic acid may comprise a wild type gene sequence that has been altered through the introduction into the gene of substitutions, mutations, insertions or deletions that alter the affinity of the compound for the RNA sequence motif. Gene fusions, that combine the two or more molecules so as to create a hybrid molecule with specific affinity for a specific RNA sequence may also be used.

The nucleic acid encoding the RNA-binding compound may be part of a gene library. In this scenario, the cDNAs representing the entire genotype of an organism are cloned into a suitable expression vector and a host strain is transformed with the vectors so that only one gene is present in each cell.

The nucleic acid may also be subjected to mutagenesis so as to create a library of different genes. The method of the present invention may then be used to identify mutations in a nucleic acid that give rise to an altered affinity in the encoded compound for a particular RNA sequence motif.

The candidate nucleic acid should ideally be cloned under the control of an inducible promoter, so that the system is easily manipulable. Transcription of the RNA-binding compound can then be controlled to coincide with the desired stage of growth of the host cell population.

Suitable inducible promoters are well known to those of skill in the art (see, for example, Sambrook et al., 1989; Molecular cloning; Cold Spring Harbor Laboratory Press). In yeast, the promoter of choice for the expression of the candidate nucleic acid is the PGK/GAL promoter. This promoter is silent in the presence of glucose in the growth medium, but when this sugar is replaced by galactose, expression of the RNA binding compound is induced.

The RNA sequence motif that forms the binding site for the compound of interest should be known in order that it can be introduced into the mRNA of the nucleic acid that codes for the fluorescent marker. However, the motif may be putative or hypothetical: it need not be known that any compound actually does interact with RNA containing this sequence. For example, it may be that a common consensus sequence found in an RNA species is hypothesised to represent a binding site. The method of the present invention then allows this theory to be accurately assessed. If the sequence is found to cause a decrease in the translation of the marker gene, then those cells in which lower translation levels are evident can be analysed for the presence of the nucleic acid of interest.

The sequence motif of interest may be inserted anywhere in the transcribed region of the nucleic acid that encodes the fluorescent marker protein. Preferably, the insertion site is in the 5' or 3' untranslated region (UTR) of the mRNA for the marker gene. Most preferably, the insertion site is in the Cap-proximal region of the 5'UTR, where it has been previously shown that binding of a protein can inhibit the access of the ribosome and so prevent efficient translation of the mRNA molecule. It is also preferable that the usual translation initiation signals that are present in the reporter mRNA are not disrupted, so that translation occurs normally in those instances when binding to the sequence motif does not occur.

The fluorescent marker protein encoded by the marker gene may be any protein whose presence in the cytoplasm of a cell causes the cell to fluoresce. Suitable proteins that are inherently fluorescent include the green fluorescent protein (GFP) that possesses a bimodal absorption spectrum and the blue-fluorescing GFP mutant (Heim et al 1994 *PNAS USA* 91, 12501–12504). Other suitable mutants of GFP include the S65T mutant that possesses a single absorption peak centred at 490 nm or the S147P mutant which emits a stronger fluorescent signal than the GFP wild type at high temperature (Kimata et al., (1997) *Biochim Biophys Res Commun* 232(1) pp69–73). When the method of the present invention is performed using yeast as host cells, the selection marker is preferably the GFP mutant S65T. This is mainly because the background fluorescence in yeast is close to the optimal wavelength at which wild type GFP fluoresces. In contrast, the GFP mutant S65T possesses ideal physical properties for use in yeast cells.

Combinations of mutants may also be used in order to tailor the physical properties of the mutant GFPs to suit the application of choice (Heim and Tsien, (1996), *Curr Biol* 6(2), p178–182; Cormack et al, (1996) *Gene*, 173(1), pp33–38).

In an alternate embodiment of the invention, the protein need not necessarily be inherently fluorescent, although in this instance its concentration must be directly related to the level of fluorescence that is visualised in the cell. For example, the protein may possess an enzymatic activity that alters the fluorescence of a substrate in the cell. A suitable technique in this respect is described by Zlokarnik et al, (1998) *Science*, 279, pp84–88. In this instance, the marker gene used is β-lactamase, the substrate for which is a membrane-permeant fluorogenic ester derivative termed CCF2/AM. This is introduced into the growth medium and will fluoresce only in cells that express β-lactamase. In those cells that contain compounds that bind to β-lactamase mRNA and thus repress its translation, lower levels of this enzyme result, so causing a lower level of fluorescence in the cell. This technique thus allows the visualisation of gene expression within the cell in the absence of a need to permeabilise the cell. The link between genotype and phenotype is thus retained, so enabling multiple enrichment steps to be performed and allowing the analysis of the selected cells' genotype.

According to a further aspect of the present invention there is provided a recombinant nucleic acid encoding an RNA molecule operably linked to a promoter, the RNA comprising: i) a sequence encoding a fluorescent marker protein or fluorescent marker peptide, and ii) a binding site for a RNA-binding compound.

Preferably the promoter is an inducible promoter such as PGK/GAL. The nucleic acid may be cloned into a plasmid vector, suitable to allow expression in the host cell of choice.

The cDNAs for suitable marker genes are available in the literature. For example, the gene sequence for GFP is published in Chalfie et al, 1994 and the β-lactamase gene has been widely known for some years (Sutcliffe et al, (1978) PNAS USA, 75, pp3737). Other suitable selection markers will be well known to those of skill in the art.

Preferably, the fluorescent marker should be cloned under the control of a constitutive promoter, such as, for example, the TEF1 promoter (translation elongation factor promoter) or alcohol dehydrogenase promoter. This ensures that any differences in the degree of fluorescence that are observed between cells are likely to be solely due to the activity of the RNA-binding compound.

Host cells suitable for use in accordance with the present invention include bacteria, yeast and eukaryotic cells. Easily manipulated bacterial species include *E. coli* or *S. typhimurium*. Yeast species such as *S. cerevisiae, S. pombe*, and *C. albicans* are particularly suited to this method. However, eukaryotic cell lines such as mammalian, amphibian or insect cells may also be used, particularly in circumstances where the presence of other proteins is necessary for the RNA binding activity of the compound of interest. For example, when the RNA binding compound requires the presence of a protein that is only found in appropriate amounts in a certain cell type, the method will need to be performed in these host cells.

The host cell of choice is yeast, more preferably *S. cerevisiae*. The reason for this preference is that yeast is a unicellular organism with a short generation time that is eukaryotic and that can thus be expected to translate and process eukaryotic proteins into their native form. Yeast cells are also very easy and inexpensive to culture and can easily be manipulated genetically. There are also a number of available marker genes such as URA3 and TRP1 that allow the initial selection of double transformants that contain both the gene for the RNA binding compound and the gene for the fluorescent marker protein. Furthermore, a number of inducible expression systems are well documented, such as that using the PGK/GAL promoter.

In the method of the invention, the nucleic acid encoding the RNA binding compound and the nucleic acid encoding the fluorescent marker protein must be co-transformed into the same host cell. The nucleic acids may be plasmid-borne, or may be integrated into the genomic DNA of the host cell. In order to allow for selection of doubly transformed host cells, both nucleic acids must be linked to a selectable marker such as an antibiotic resistance gene (such as the ampicillin resistance gene) or a metabolic enzyme (such as TRP1).

In the preparation of a strain of host cells suitable for use in accordance with the method of the present invention, the nucleic acid encoding the fluorescent marker is initially cloned into the host strain. The nucleic acids (or gene library) encoding potential RNA binding compounds is then transformed into the already-transformed strain using a second selection marker. (Obviously, these transformation steps may be performed simultaneously). In yeast, two suitable markers may be, for example, the TRP1 and URA3 selection markers. Double transformants containing nucleic acids for both the fluorescent marker protein and the RNA binding compound are then selected on media that are deficient in both tryptophan and uracil.

Any method of selection that allows the separation of non-fluorescent cells from fluorescent cells can be used to select cells expressing an RNA-binding compound that has successfully repressed translation of the fluorescent marker. The population of cells to be separated will depend upon whether repression or activation of translation is being selected for. However, in either case, the population of cells should be selected that are either more or less fluorescent than control cells. In the method of the first embodiment of the invention, control cells are cells that contain only the nucleic acid comprising the coding region for the fluorescent marker protein and the binding site for the RNA-binding compound. In the method of the second embodiment of the invention, control cells are those that contain the nucleic acid comprising the coding region for the RNA binding compound and the nucleic acid comprising the coding region for the fluorescent marker protein and the binding site for the RNA-binding compound.

Currently, the preferred technique that allows the fast quantitation of the fluorescence level of cells is flow cytometry. The most suitable technique for clonal selection of the cells of interest is fluorescence-activated cell sorting (FACS) that allows high-throughput screening of large numbers of cells. Furthermore, this procedure allows the recovery of living cells after sorting, meaning that multiple rounds of sorting may be performed in order to enrich for the cells of interest. The FACS technique has been shown to be applicable to most cell types, including yeast (Atkins et al, (1995) *Curr Genet*, 28(6) pp585–588), the host cell of choice in the method of the present invention.

FACS is normally used to select for cells that exhibit higher than average levels of fluorescence, although may be easily adapted to select cells exhibiting lower than average fluorescence levels. The method of the present invention necessitates the selection of cells that exhibit altered levels of fluorescence relative to the mean fluorescence level in the cell population, since it is these cells in which the level of translation of the fluorescent protein has been altered. These cells may express RNA binding compound s that have successfully bound to the sequence motif in the mRNA of the marker compound and that have thus altered translation of the fluorescent marker protein.

Preferably, the method of the present invention is designed so that translation of the mRNA encoding the fluorescent marker protein is repressed, through the interaction of a RNA binding compound and the RNA sequence motif that is present in the mRNA of the fluorescent marker protein. This interaction prevents the access of the translation machinery to the RNA binding site and thus causes a decrease in the level of translation from this mRNA species.

Preferably, the level of fluorescence is altered by at least 10%, more preferably 20–50%, most preferably greater than 50% relative to the mean fluorescence of the ell population. Most preferably, the level of fluorescence is lowered by this amount relative to the me an level in the host cell population.

It has also been found, surprisingly, that for the method of the present invention to be efficacious in correctly identifying cells that contain RNA binding compounds with specificity for the RNA sequence motif of interest, it is necessary to use multiple cycles of enrichment. It has been found that using just one selection step results in the identification of a large number of "false positive" clones, that do not possess RNA binding compounds that bind to the binding site of interest. Hence, it has been found necessary to culture the cells selected in the selection step in order to expand the selected population. The cells are then subjected to a compound of selection, using, for example, FACS. Preferably, at least three iterative cycles of culture and selection are performed.

In selecting cells displaying lowered levels of fluorescence, minimally-fluorescent cells are also selected. This population of cells is contaminated by cells that harbour mutations in the marker gene or that have lost the marker gene through deletion of the gene or loss of the plasmid, despite culture in selective medium.

In order to take this population of cells into account, the pool of minimally fluorescent cells that is selected in the final selection step is split into a number of groups, in decreasing order of fluorescence. Preferably, in order to strike a compromise between the least degree of work involved and the greatest efficiency of selection of positive clones, the final pool of cells is split into around five groups. It has been found that the group exhibiting the lowest fluorescence (group 5) includes deletants and revertants that have lost the marker gene. However, the population of cells displaying reduced but not minimal fluorescence (group 4) has been found to contain the greatest enrichment for RNA binding compounds of interest.

Additionally, the use of multiple cycles of enrichment allows counterselection against non-specific, constitutive loss of the marker gene, since when using an inducible system for the expression of candidate nucleic acids encoding the RNA binding compound, cells that display a specific reduction in fluorescence will shift to and can be recovered from the high fluorescent pool following incubation in glucose-containing medium (under conditions in which the candidate nucleic acids are not expressed).

Once the final pool of cells has been isolated, cells that display a non-specific reduction in fluorescence that is not due to the presence in the cell of a RNA-binding compound that exhibits specific affinity for the sequence motif of interest are removed by shifting to glucose-containing medium. The genotype of the remaining population of cells can then be analysed. Suitable methods will be well known to those of skill in the art and will include the sequencing of the nucleic acid that encodes the RNA-binding compound. It may be that this nucleic acid can then be subjected to mutagenesis, so creating a library of mutagenised nucleic acids. This library can then be used once again in the method of the present invention to select for compounds with altered affinity for the RNA sequence motif.

In the case of a proteinaceous RNA binding compound, the protein or peptide could be purified and further analysed. For example, the protein may be used in structure/function studies in order to aid the rational design of mimetics that bind to the same site in RNA. Suitable methods of analysis are now routine in the art and will be readily apparent to the skilled man.

According to a preferred aspect of the present invention there is provided a method for the isolation of a nucleic acid coding for a RNA-binding compound, said method comprising the steps of:

a) expressing in a yeast cell
   i) one or more candidate nucleic acids to be screened for coding for the RNA binding compound, wherein each candidate nucleic acid comprises a coding sequence operably linked to a promoter inducible in said yeast cell, and
   ii) a nucleic acid comprising a coding region for a GFP mutant that detectably fluoresces at a wavelength distinguishable from wild type GFP, wherein the nucleic acid coding for the GFP mutant comprises a constitutive promoter that is operably linked to the coding sequence and includes in the 5' untranslated region a binding site for the RNA-binding compound, b) selecting by FACS a yeast cell that exhibits a lowered level of fluorescence from levels in a yeast cell containing ii) alone; and c) isolating the nucleic acid coding for the RNA binding compound from the selected cell.

According to a further aspect of the invention there is provided a kit comprising in one or more containers a recombinant nucleic acid encoding an RNA molecule operably linked to a promoter, said RNA molecule comprising: i) a sequence encoding a fluorescent marker protein or peptide, and ii) a binding site for a RNA-binding compound. The kit may further comprise one or more candidate nucleic acids each of which comprises a coding sequence operably linked to a promoter, for screening for a RNA-binding compound. The candidate nucleic acids may comprise a cDNA library.

According to a still further embodiment of the invention there is provided the use of a recombinant nucleic acid as described above, optionally contained within a host cell, in a method according to the invention, as described in detail above.

Various aspects and embodiments of the present invention will now be described in more detail by way of example, with particular reference to a system in which yeast cells are used as hosts for expression of the candidate and marker nucleic acids. It will be appreciated that modification of detail may be made without departing from the scope of the invention.

DESCRIPTION OF THE FIGURES

FIG. 1: illustration of the functional principle of TRAP in a yeast expression system FIG. 2: Description of the plasmids used.

FIG. 3: Sequences and nomenclature of the GFP reporter plasmids (SEQ ID NOS.3–9).

EXAMPLES

Materials and Methods

Plasmid Construction

Figure 4A:
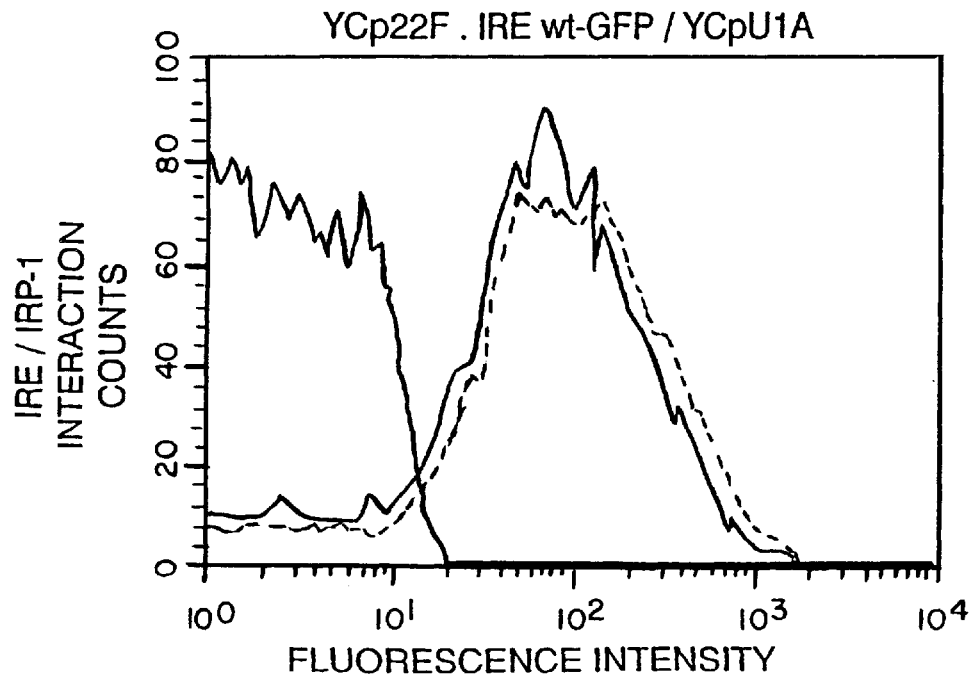
FIGS. 4A–4F: Isolation of cells expressing cognate RNA-binding proteins by FACS.

Green fluorescent protein indicator plasmids YCp22F.bs-GFP are driven by the TEF1 (translation elongation factor) promoter and contain the TRP1 selection marker. For the construction, the corresponding YCp22FL plasmids (Stripecke et al., 1994; Oliveira et al, 1993) were digested with NdeI, the NdeI cohesive ends were filled in using Klenow fragment of E. coli DNA polymierase I, prior to a further digestion with XbaI and gel purification using QIAquick columns (Qiagen). The Ser65->Thr mutant GFP coding sequence was amplified by PCR (Boehringer Mannheim PCR Master kit) with primers 5'-TTTTTAATT ATGAGCAAAGGAGAAGAAGAACTTTTC-3'(SEQ ID NO.1) and 5'-TTTTTTCTAGATTATTTGTATAGT TCATCCATG-3'(SEQ ID NO.2), digested with XbaI, and then introduced into the NdeI blunted-XbaI plasmids to create plasmids YCp22F.IREwt-GFP, YCp22F.IREmt-GFP, YCp22F.U1Awt-GFP, YCp22F.U1Amt-GFP, YCp22F.MSC-GFP, YCp22F.MSA-GFP, YCp22F.MSAdel-GFP.

Plasmids YCpIRP-1 (described a s YCpIRF by Oliveira et al. 1993), YCpU1A (Stripecke et al., 1994) and YCpCP express IRP-1, U1A and MS2 coat protein, respectively, under the control of the PGK:AL fusion promoter and contain URA3 as a selection marker.

Yeast Culture Conditions and Preparation of Protein Extracts

The Saccharomyces cerevisiae haploid strain RS453 (ade 2-1, trp 1-1, leu 2-3, his 3-11, ura 3-52, lys+, can 1-100) was grown at 30° C. in YPD medium (1% peptone/1% yeast extract/2% glucose) or YPD-agar plates. The yeast selective defined media (SD) contained 0.67% (w/v) yeast nitrogen base without amino acids, 2% glucose or 2% galactose, amino acids and nucleotides as follows: adenine 20 mg/l; arginine 20 mg/l; histidine 20 mg/l; leucine 60 mg/l; tryptophan 20 mg/t and uracil 20 mg/l. Solid defied media preparation followed exactly the protocol above with the addition of 2% agar.

Yeast transformation was performed by the lithium acetate method (Ito et al., 1983). For the mixed plasmid transformation, YCpIRP-1 and YCpU1A were mixed in a 1:500,000 ratio. DNA concentration was estimated by measuring the absorption at 260 nm and by ethidium bromide staining.

The mixed plasmids were used to transform RS453 cells carrying plasmid YCp22F.IREwt-GFP. Transformants were selected on plates lacking tryptophan and uracil. Approximately $3\times10^6$ transformants were pooled in liquid selective medium and used for sorting the cells expressing IRP-1, as described below.

For induction of the GAL promoter, cultures were grown overnight in SD containing 2% galactose. Yeast protein extracts were prepared as follows: yeast cultures of 10–20 ml were harvested by centrifugation. The pellet was washed once with 10 ml sterile distilled water and resuspended in 1 ml yeast lysis buffer (100 mM NaCl, 50 mM Tris-HCl, pH 7.4). The cell suspension was briefly centrifuged again and resuspended in 150 ml of lysis buffer containing 1 mM PMSF, 10 mg/ml leupeptin, 1 mM dithiothreitol. Cells were disrupted with glass beads (0.45–0.50 mm) at 4° C. by three cycles of 1 min vortexing and 1 min incubation on ice, followed by centrifugation for 2 min at 6000 g in a microfuge. The supernatant was centrifuged again for 5 min at 1500 g, transferred into a fresh tube and stored at –80° C. The protein concentration of the extracts was determined using the Bio-Rad protein assay (Bio-Rad Laboratories GmbH).

Gel Retardation Assays $^{32}$P-labeled IRE and U1snRNA loop 2 probes (specific activity ~$2.9\times10^7$ cpm/mg RNA) were synthesized in vitro from XbaI linearised plasmids IREwt-CAT (Gray et al, 1993) and U1Awt-CAT (Stripecke and Hentze, 1992) with T7 RNA polymerase (Stratagene). Aliquots (10 to 40 mg each) of yeast extracts were incubated for 20 min at room temperature for IRP-1 or ice for U1A with 1 ng of probe in 10 ml lysis buffer. Subsequently, samples were incubated for 10 min with heparin (0.5 mg/ml) and analyzed by non-denaturing gel electrophoresis (Leibold and Munro, 1988).

Fluorescence Activated Cell Analysis and Sorting

A Facscan (Becton Dickinson) flow cytometer was used to analyze the fluorescence levels of cells. The Facscan uses an argon ion laser fixed at 488 nm for excitation and a 530 nm bandpass filter for collection of the emitted fluorescence. Measurements were made of the cell size, internal complexity and relative fluorescence intensity of single cells. Debris were excluded from the analysis by gating on the Forward Scatter versus Side Scatter parameters.

For sorting, the cells were analysed and isolated on a Facs Vantage (Becton Dickinson) cell sorter. Excitation was at 488 nm and the emitted fluorescence collected with a 530 nm bandpass filter. Sorting gates were set using Forward Scatter Width versus Side Scatter Height signals, to exclude debris and clumps, and Forward Scatter Height versus Fluorescence Height signal, to sort cells that fell within a certain fluorescence intensity.

Example 1

Using well-characterised RNA-protein interactions that are known to occur in the following systems, it is demonstrated herein that the method of the present invention allows the rapid and specific identification of RNA-protein interactions in vivo and allows the cloning of cDNAs encoding a specific, cognate RNA-binding protein. The interactions used herein are the binding of the spliceosomal protein U1A to loop 2 of U1snRNA (Scherly, D., Boelens, W., van Venrooij, W. J., Dathan, N. A., Hamm, J. & Mattaj, I. W. (1989) EMBO J. 8, 4163–4170), the binding of iron regulatory protein (IRP)-1 to iron-responsive elements (IREs) (Hentze, M. W. & Kühn, L. C. (1996) Proc. Natl. Acad. Sci. USA 93, 8175–8182) and the binding of bacteriophage MS2 coat protein to the MS2 replicase mRNA (. Lowary, P. T. & Uhlenbeck, O. C. (1987) Nucl. Acids Res. 15, 10483–10493; Witherell, G. W., Gott, J. M. & Uhlenbeck, O. C. (1991) Progress on Nucl. Acids Res. & Mol. Biol. 40, 185–220).

Example 2

The Principle of the Translational Repression Assay Procedure

FIG. 1 outlines the functional principle of TRAP in a yeast expression system. RS453 cells are transformed with the GFP indicator plasmid that carries within the GFP 5'UTR the binding site of the protein under study and the plasmid for expression of the RNA-binding protein (or a cDNA library) under the control of a galactose-inducible promoter. In galactose medium, expression of the RNA-binding protein is induced.

The RNA-protein interaction at the 5' end of the GFP mRNA represses its translation and the fluorescence of the cell is diminished (cognate interaction). GFP mRNA translation yields high fluorescence levels when expression of the RNA-binding protein is repressed in glucose medium (no binding protein expression), or when the expressed protein cannot interact with the GFP mRNA (non-cognate binding protein or mutated binding site).

RS453 cells (genotype ade 2-1, trp 1-1, leu 2-3, his 3-11, ura 3-52, lys+, can 1-100) were transformed with plasmids for the expression of the RNA-binding protein (or a cDNA expression library) from a galactose-inducible promoter (that is repressed in the presence of glucose), and the GFP indicator (18) bearing the protein binding site in the 5'UTR of the encoded mRNA from a constitutively active promoter. Both plasmids are centromeric and are maintained at 1–2 copies per cell.

In the presence of glucose, GFP is expressed and yields high fluorescence levels. Replacement of glucose by galactose in the growth medium activates the PGK/GAL promoter, and the expression of the RNA-binding protein is induced. As a consequence, GFP expression is translationally inhibited and the fluorescence level of the cells bearing the cDNA expression vector for the cognate binding protein is diminished. This can be quantitated by flow cytometry, cells displaying different GFP levels can be separated by fluorescence activated cell sorting (FACS), and viable cells recovered for further analysis or additional cycles of sorting.

Example 3

Specificity of TRAP

The specificity of TRAP was challenged with two well-characterised RNA-protein interactions: the IRE/IRP-1 and the U1 snRNA loop 2/U1A interactions. The coding sequence for the S65T mutant GFP [which displays improved excitation/emission characteristics for fluorimetry and FACS (Heim et al., 1995; Cubit et al, 1995)] was subcloned into reporter gene plasmids to generate YCp22F.IREwt-GFP, YCp22F.IREmt-GFP, YCp22F.U1Awt-GFP and YCp22F.U1Amt-GFP.

Yeast cells were co-transformed with one of these GFP reporter plasmids and either YCpIRP-1 or YCpU1A. These plasmids are described in FIG. 2. The GFP reporter plasmids YCp22F.BS-GFP contain the GFP S65T mutant open reading frame. The IRE and U1 snRNA loop 2 wild type and mutated and the MSC and MSA binding sites (BS) are cloned into the AflII site. The binding sites are located 9 nucleotides downstream from the transcription start site and 32 nucleotides upstream from the GFP translation initiation codon. The plasmids harbour a TRP1 selection marker.

YCpU1A, YCpIRP-1 and YCpCP were used for the galactose inducible expression of U1A, IRP-1 and MS2 coat protein, respectively. These plasmids contain a URA3 selection marker. The sequences and nomenclature of the GFP reporter plasmids are described in FIG. 3. Binding site insertions are represented by Capital letters. Differences between wild type and mutated binding sites are indicated by arrows.

Double transformants were selected on plates lacking tryptophan and uracil, grown in selective liquid medium containing either 2% glucose or 2% galactose for 14 hours to a density of OD600 0.5–1, and GFP fluorescence analysed by flow cytometry. FIG. 4 shows that the fluorescence of GFP-expressing cells is specifically reduced by cognate RNA-protein interactions. The fluorescence of cells grown in glucose is shown by the light-shaded curves or in galactose by the dark-shaded curves. Control cells not carrying a GFP plasmid are represented by the dark black curves in panels a and d. The fluorescence intensity is plotted against counts (number of cells analysed per channel of fluorescence).

Figure 4D:
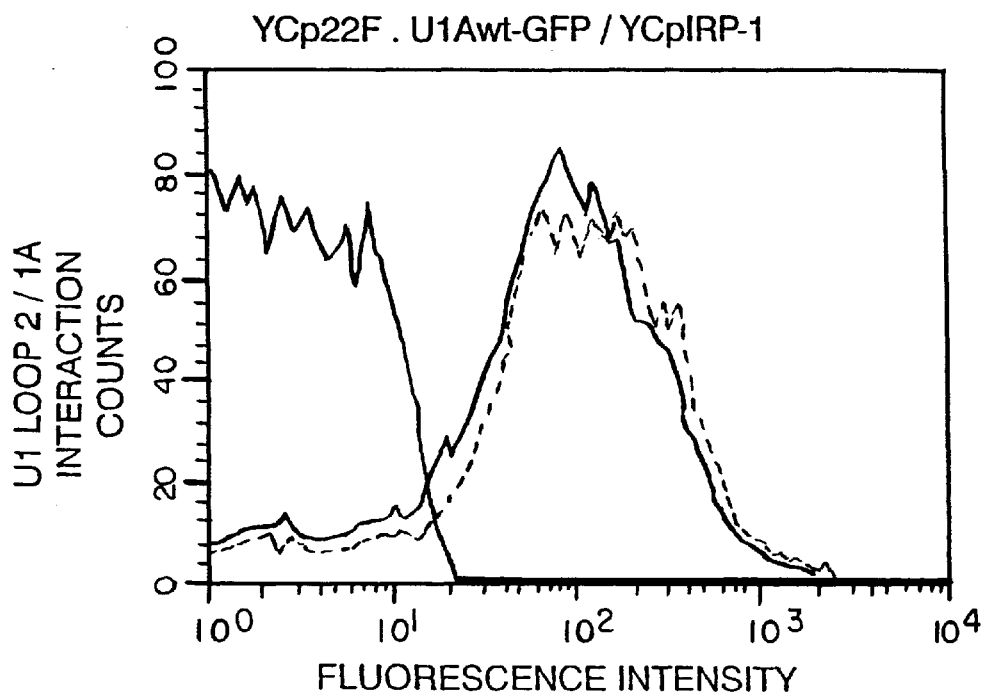
Figure 4:
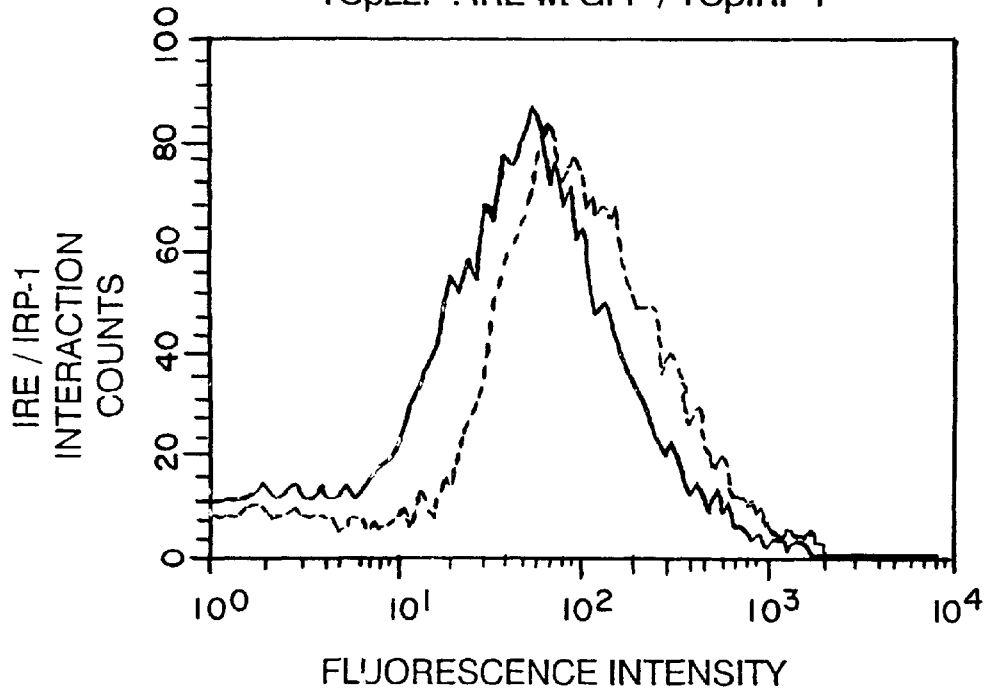
Figure 4:
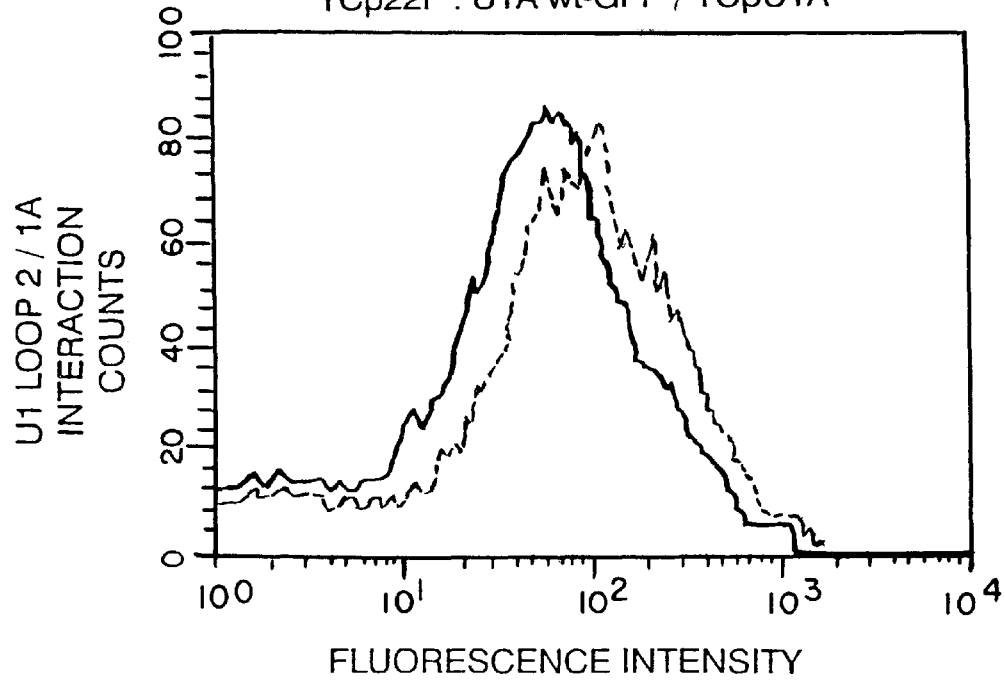
Figure 4:
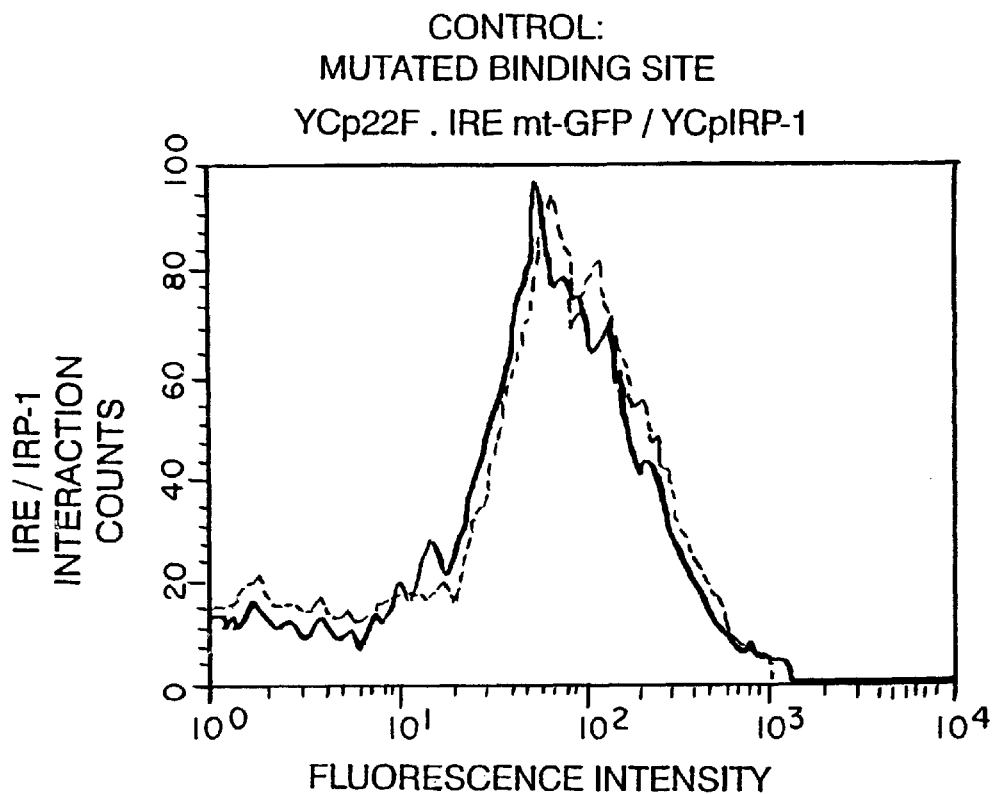
Figure 4:
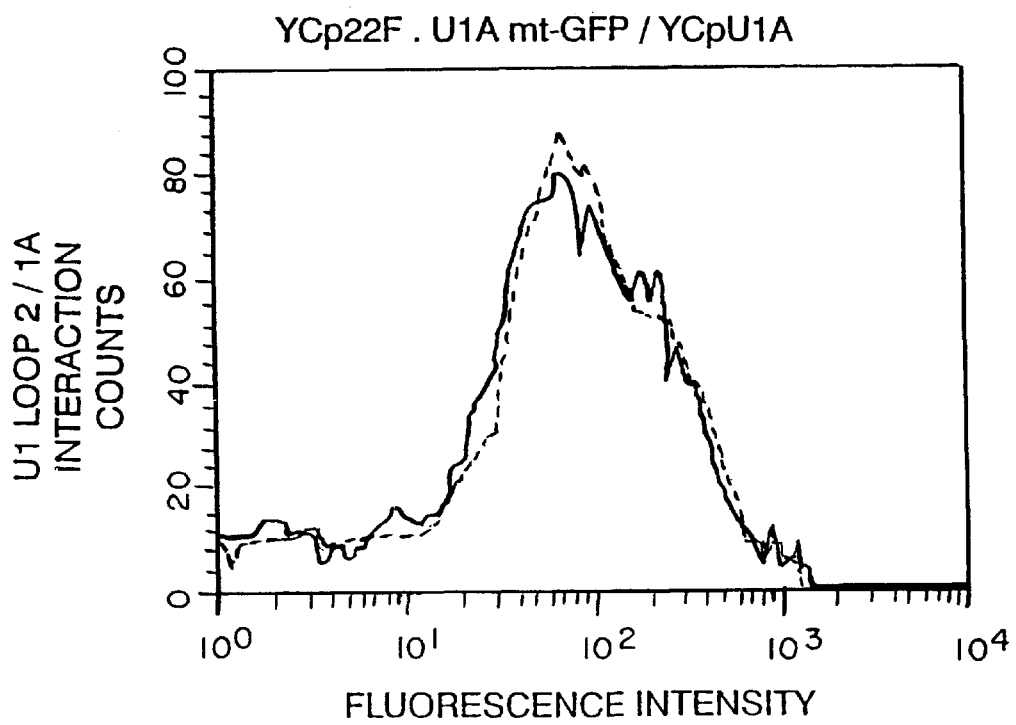

These results show that cells grown in glucose and expressing GFP from YCp22F.bs-GFP plasmids display high fluorescence compared to control cells lacking a GFP reporter plasmid (FIGS. 4a and 4d). Induction of the cognate RNA-binding proteins in galactose-containing media significantly decreases the mean fluorescence, manifested by a leftward shift of the fluorescence distribution curve towards lower values (FIGS. 4b and 4e) and the repression of the mean fluorescence of cells (Table 1). This reduction specifically requires the presence of the wild type binding site and the cognate binding protein, and is not seen with either the mutant binding sites (FIG. 4c and f) or the non-cognate binding proteins (FIGS. 4a and d).

TABLE 1

Quantitative analysis of the repression of GFP fluorescence by RNA-protein interactions with different binding affinities

| INTERACTION | APPROX. AFFINITY (REFERENCES)* | GFP REPRESSION† |
| --- | --- | --- |
| IRE/IRP-1 | 1.0–10 nM | ~60–70% |
| U1 loop 2/U1A | 0.02–80 nM | ~40% |
| MSC/MS2 coat protein | 0.02–0.1 nM | ~70% |
| MSA/MS2 coat protein | 0.1–1 mM | ~50% |

*Binding affinities for the different RNA-protein interactions as reported in the literature.
†GFP fluorescence of cells grown in glucose media was defined as 100%. The remaining mean fluorescence of cells after growth in galactose media was expressed as a percentage of the above, and the repression level calculated by subtraction from 100%.

As shown in Table 1, the IRE/IRP-1 (Leibold et al., 1990; Bettany et al., 1992; Henderson et al, 1994) and U1 loop 2/U1A complexes (Lutz-Freyermuth et al, 1994; Jessen et al., 1990; Stump et al., 1995) that repress GFP translation significantly have high binding affinities (nanomolar range). The affinity required for an RNA/protein complex to repress GFP mRNA translation was further investigated with the MSC and MSA (in decreasing order of affinity) binding site/MS2 coat protein interactions (Lowary and Uhlenbeck, 1987; Witherell et al, 1991).

Plasmids YCp22F.MSC-GFP and YCp22F.MSA-GFP (FIGS. 2 and 3) were generated as described above. Yeast cells were co-transformed with one of the two GFP reporter plasmids and plasmid YCpCP (FIG. 2). Induction of the coat protein in galactose-containing media resulted in the repression of GFP expression (Table 1). Even the lower affinity MSA/MS2 coat protein complex reduced mean cell fluorescence significantly, indicating that an affinity at the micromolar range is enough for the formation of an RNA/protein complex that can be detected by TRAP. The MSA mutant binding site conferred a relatively lower degree of repression compared to the MSC binding site that has a higher affinity for the MS2 coat protein. Thus, the extent of GFP fluorescence repression was influenced by the affinity of the RNA-protein interaction.

Example 4

Isolation of Cells Expressing Cognate RNA-binding Proteins by Fluorescence-activated Cell Sorting The specific reduction of GFP fluorescence that was caused by the interaction of cognate RNA-binding proteins whose wild type binding sites had been introduced into the 5'UTR of GFP reporter mRNAs (FIG. 4) suggested that it is possible using FACS to recover cells expressing the cognate RNA binding protein from a background pool of cells expressing control proteins.

Cells co-transformed with plasmid YCp22F.IREwt-GFP and either YCpIRP-1 or YCpU1A were mixed at a ratio of 1:10,000. The mixed cell suspension was grown in galactose-containing medium to induce the expression of the RNA-binding proteins, and sorted by FACS according to the GFP fluorescence of the cells. Cells displaying low fluorescence levels were regrown in galactose medium and sorted for a second time.

Figure 5:
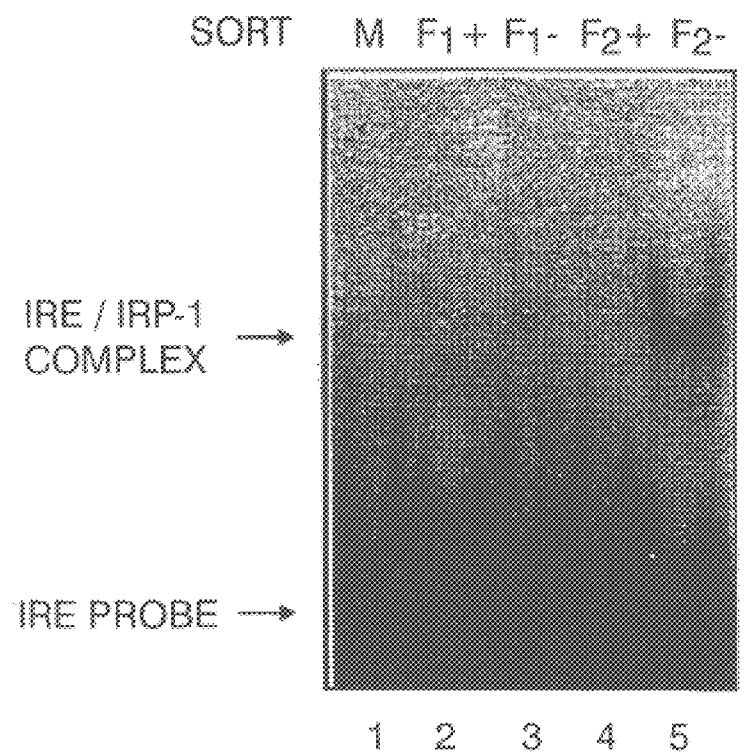
FIG. 5: Gel retardation assay for IRE binding assay using extracts from sorted cells.

The enrichment for cells carrying plasmid YCpIRP-1 was tested in a gel retardation assay for IRE-binding activity using extracts prepared from sorted cells. The results are shown in FIG. 5. Total cell extracts were incubated with 1 ng IRE probe and analysed by native PAGE. After two rounds of sorting (F2), the extracts from galactose-induced cultures of cells selected for low fluorescence levels (H, lane 5) display IRE-binding activity comparable to that of an extract of IRP-1 expressing cells and U1A expressing cells mixed at a ratio of 1:100 (not shown). No binding activity was detectable in the initial 1:10,000 starting population (M, lane 1), in extracts from cells selected for high fluorescence levels (+, lanes 2 and 4), or sorted only once (F1-, lane 3).

Figure 6:
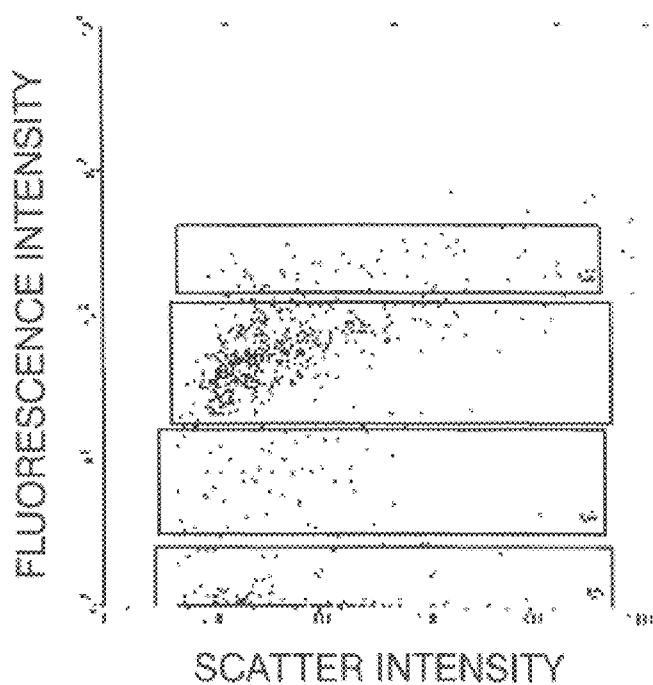
FIG. 6: Graph showing the four different pools of cells exhibiting varying levels of fluorescence.
Figure 7:
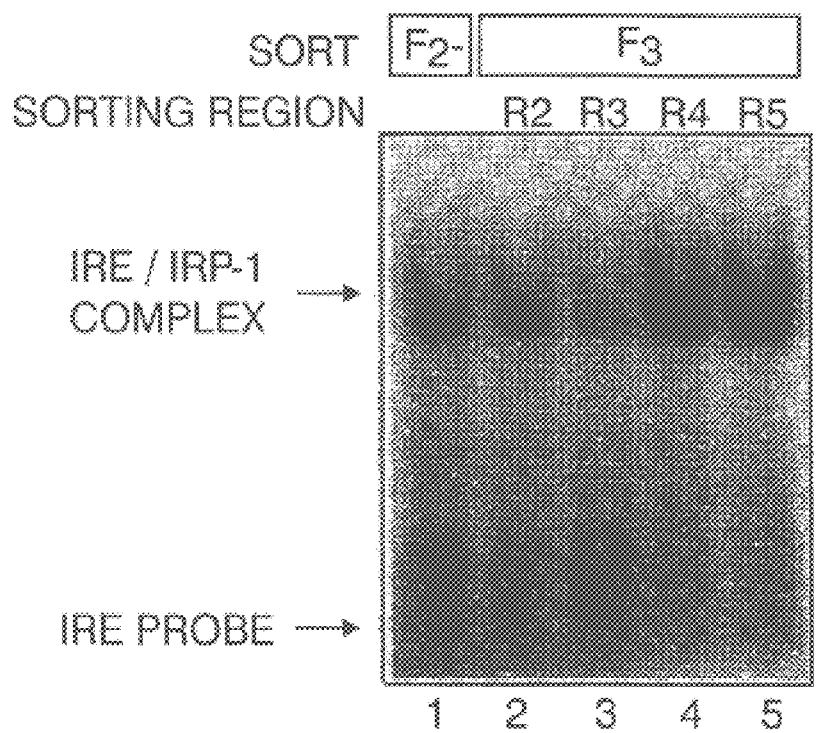
FIG. 7: Gel retardation assay for pools R2-R5, showing enrichment of IRE-binding activity.
Figure 8:
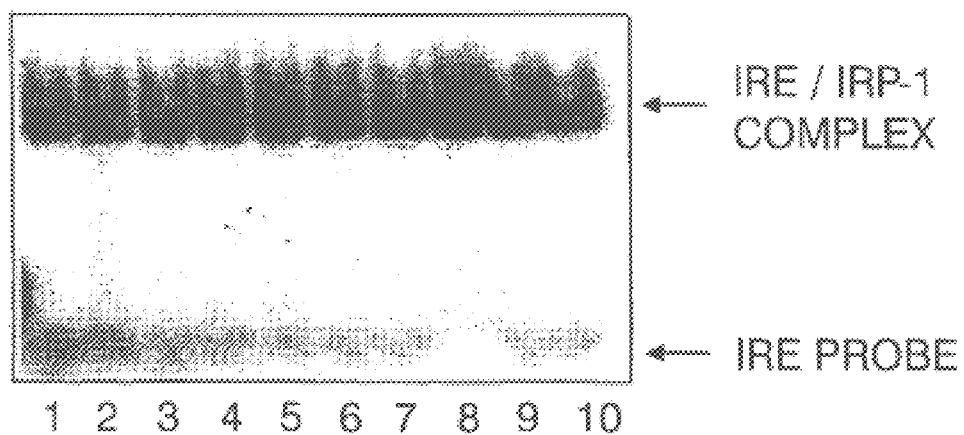
FIG. 8: Analysis of IRP-I expression in selected cells.
Figure 9:
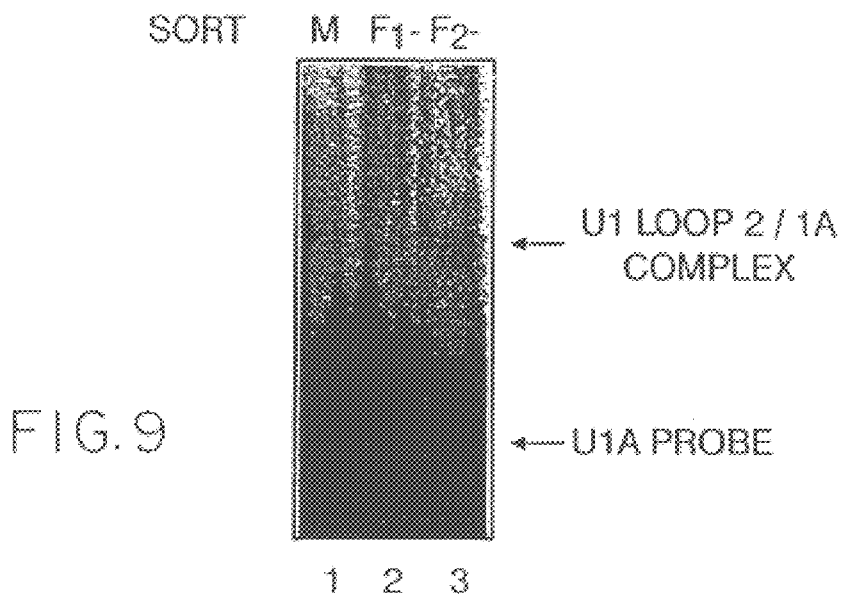
FIG. 9: Gel retardation assay for U1 loop2 binding assay using extracts from sorted cells.
Figure 10:
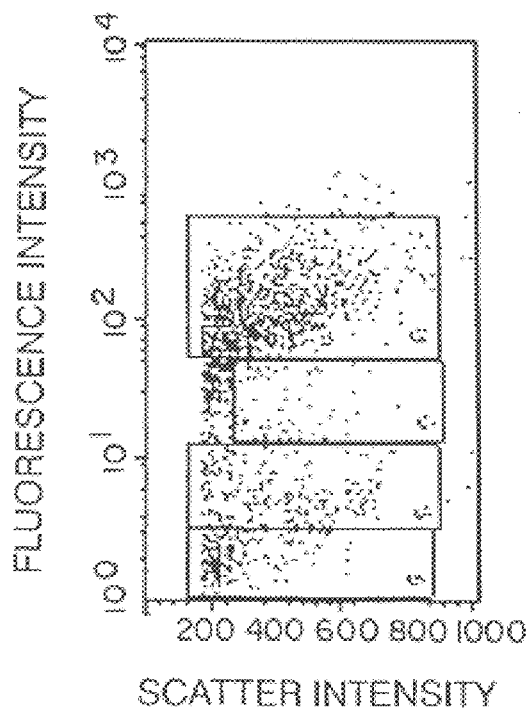
FIG. 10: Graph showing the four different pools of cells exhibiting varying levels of fluorescence.

The F2-cells were subsequently regrown and sorted again (F3) into four different pools of descending fluorescence (R2–R5, FIG. 6). R2–R5 extracts were compared in a gel retardation assay to the F2-extracts (FIG. 7). A substantial further enrichment in IRE-binding activity is apparent in cell populations exhibiting low fluorescence, R4 (lane 4) and R5 (lane 5). Cells from culture R4 were plated on selective medium, single colonies were picked and extracts were made from cultures of these clones tested for IRP-1 expression FIG. 8). Ten out of ten clones tested from R4 expressed IRP-1 (FIG. 8). Thus, starting from 1:10,000 (0.01%) cells carrying plasmid YCpIRP-1, the IRP-1 expressing cells represented 100% of the cells analysed from F3/R4.

Figure 11:
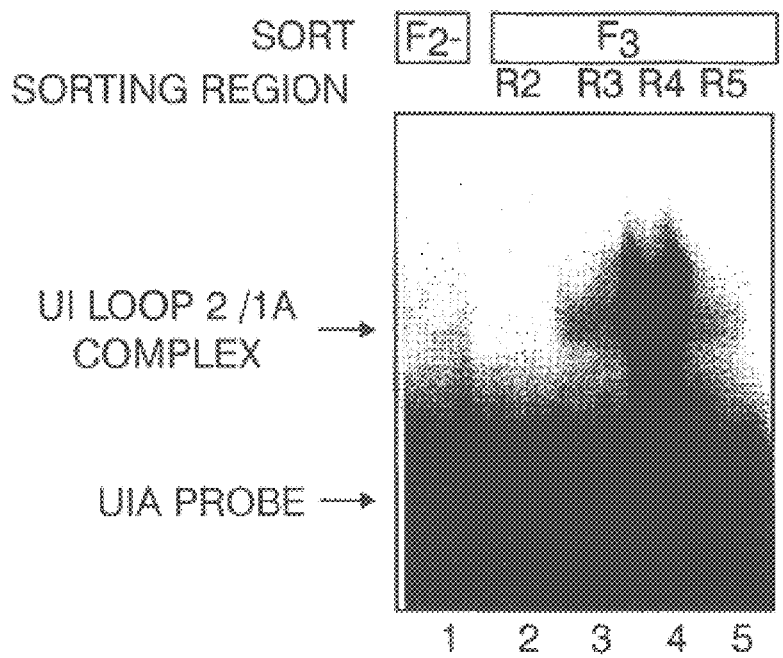
FIG. 11: Gel retardation assay for pools R2-R5, showing enrichment of U1A-binding activity.
Figure 12:
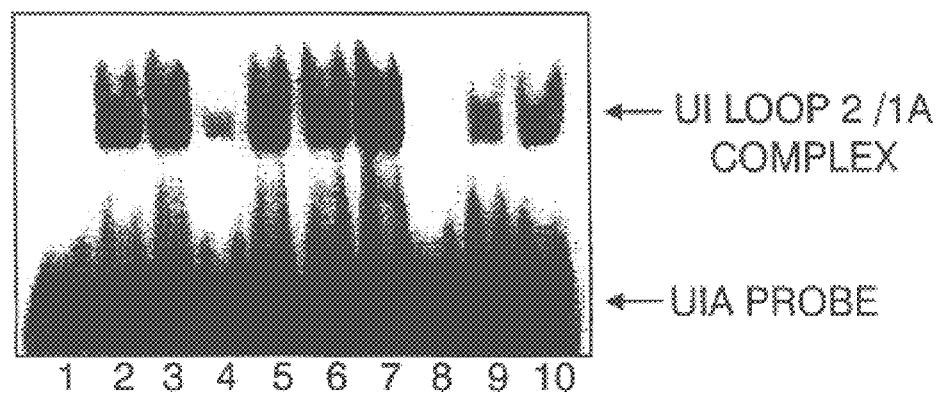
FIG. 12: Analysis of U1A expression in selected cells.

An analogous experiment was then performed for the U1A-encoding plasmid with YCp22F.U1Awt-GFP, using a 10,000-fold excess of YCpIRP-1 as a background (FIGS. 9–12). After two rounds of initial sorting (F1, F2, FIG. 9), the F2-cells were regrown and sorted into regions (F3, R2–R5, FIG. 10). As before, the strongest enrichment was observed in R4, but there was substantially less U1A activity in R3 and R5 (FIG. 11). Single colony analysis of F3/R4 revealed successful cloning of YCpU1A in eight out of ten samples tested (FIG. 12).

Taken together, the results obtained for IRP-1 and U1A underscore the potential of TRAP to be used for the identification and recovery of cells expressing an RNA binding compound from a population of cells expressing unrelated compounds.

Example 5

Cloning by TRAP

To further challenge the utility of the method of the present invention for cloning, we attempted to reclone the IRP-1 cDNA. To mimic the cloning process with a precisely preset required enrichment factor, we mixed the plasmids YCpIRP-1 and YCpU1A in a 1:500,000 ratio and transformed RS453 cells carrying YCp22F.IREwt-GFP. Double transformants were selected on plates lacking tryptophan and uracil, ~3×10$^6$ transformants were pooled, expanded in selective medium containing galactose to induce expression of the binding proteins, and sorted by FACS.

Figure 13:
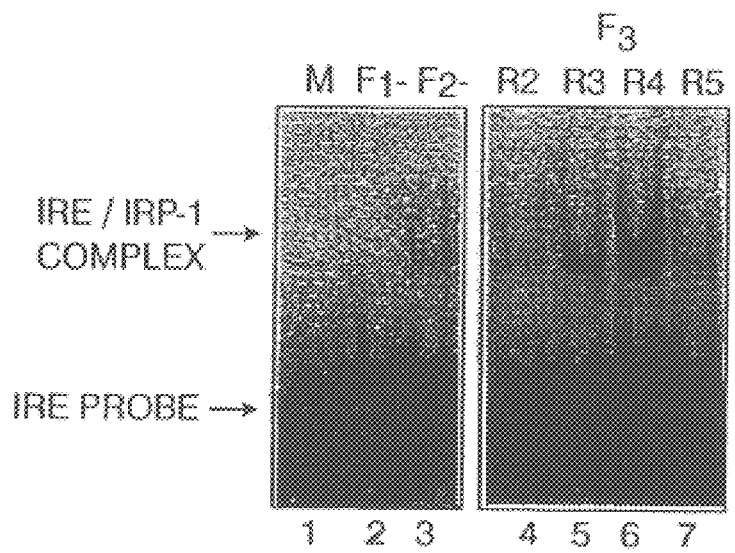
FIG. 13: Gel retardation assay showing IRE-binding activity of sorted cells.
Figure 14:
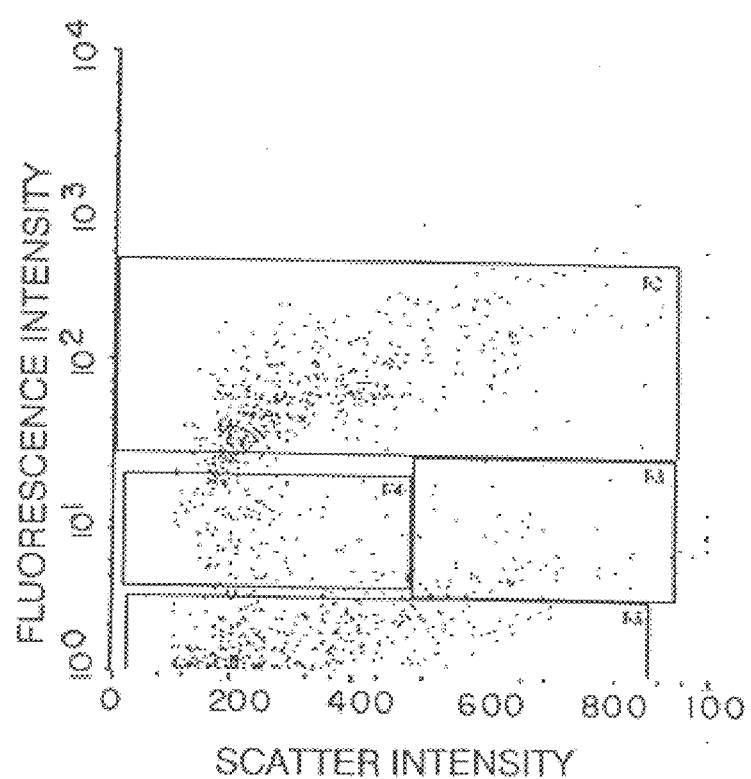
FIG. 14: Graph showing the different pools of cells exhibiting varying levels of fluorescence.

After two rounds of sorting, cells from culture F2-showed IRE-binding activity (FIG. 13, lane 3). F2-cells were further sorted into regions of cells with different fluorescence (FIG. 14), and the greatest further enrichment was again found in R4 (FIG. 13, lane 6). When single colonies from F3/R4 were analysed, one out of twenty expressed IRP-1 (not shown). Thus, TRAP allowed successful recloning of the cDNA encoding a cognate RNA-binding protein from a 500,000-fold background.

REFERENCES

Atkins et al, (1995) *Curr Genet*, 28(6) pp585–588.
Bettany, A. J. E., Eisenstein, R. S. & Munro, H. N. (1992) *J. Biol. Chem.* 267, pp16531–16537.
Chu et al., (1993) *P.N.A.S. USA* 90 pp517–521.
Cormack et al, (1996) *Gene* 173(1) pp33–38.
Cubit, A. B., Heim, R., Adams, S. R., Boyd, A. E., Gross, L. A. & Tsien, R. Y. (1995) *Trends Biochem. Sci.* 20 pp448–455.
Dabeva and Warner, (1993) *J. Biol Chem* 268 pp19669–19674.
Gray, N. K. & Hentze, M. W. (1994) *EMBO J* 13 pp3882–3891.
Gray, N. K., Quick, S., Goossen, B., Constable, A., Hirling, H., Kühn, L. C. & Hentze, M. W. (1993) *Eur. J Biochem.* 218 pp657–667.
Harada, K., Martin, S. S. & Frankel, A. D. (1996) *Nature* 380 pp175–179.
Heim and Tsien, (1996), *Curr Biol* 6(2) pp178–182.
Heim et al 1994 *PNAS USA* 91, 12501–12504.
Heim, R., Cubitt, A. B. & Tsien, R. Y. (1995) *Nature* 373 pp663–664.
Henderson, B. R., Menotti, E., Bonnard, C. & Kuhn, L. C. (1994) *J Biol. Chem* 269, pp17481–17489.
Hentze, M. W. & Kuhn, L. C. (1996) *Proc. Natl. Acad. Sci. USA* 93, pp8175–8182.
Ito, H., Fukuda, Y., Murata, K. & Kimura, A. (1983) *J Bacteriol.* 153, pp163–168.
Jain, C. & Belasco, J. G. (1996) *Cell* 87 pp 15–125.
Jessen, T. H., Oubridge, C., Hiang Teo, C., Pritchard, C. & Nagai, K. (1991) *EMBO J*. 10, pp3447–3456.
Kimata et al., (1997) *Biochim Biophys Res Commun* 232(1) pp69–73.
Laird-Offringa, I. A. & Belasco, J. G. (1995) *Proc. Natl. Acad Sci. USA* 92, pp11859–11863.
Leibold, E. A. & Munro, H. N. (1988) *Proc. Natl. Acad Sci. USA* 85, pp2171–2175.
Leibold, E. A., Laudano, A. & Yu, Y. (1990) *Nucl. Acids Res.* 18, pp1819–1824.
Lowary, P. T. & Uhlenbeck, O. C. (1987) *Nucl. Acids Res.* 15, pp10483–10493.
Lutz-Freyermuth, C., Query, C. C. & Keene, J. D. (1990) *Proc. Natl. Acad. Sci. USA* 87, pp6393–6397.
Merrick (1992) *Microbiol Rev* 56 pp291–315.
Oliveira, C. C., Goossen, B., Zanchin, N. I. T., McCarthy, J. E. G., Hentze, M. W. & R. Stripecke (1993) *Nuncl Acids Res.* 21, pp5316–5322.
Ostareck-Lederer et al (1994) *EMBO J* 13 pp1476–1481.
Putz, U., Skehel, P. & Kuhl, D. (1996) *Nucl. Acids Res.* 24, pp4838–4840.

Sachs (1993) *Cell* 74 pp413–421.
Scherly, D., Boelens, W., van Venrooij, W. J., Dathan, N. A., Hamm, J. & Mattaj, I. W. (1989) *EMBO J* 8, pp4163–4170.
SenGupta, D. J., Zhang, B., Kraemer, B., Pochart, P., Fields, S. & Wickens, M. (1996) *Proc. Natl. Acad. Sci USA* 93, pp8496–8501.
Stripecke, R. & Hentze, M. W. (1992) *Nucl. Acids Res.* 20, pp5555–5564.
Stripecke, R. (1993) *Nucl Acids Res* 21, pp5316–5322.
Stripecke, R., Oliveira, C. C., McCarthy, J. E. G. & Hentze, M. W. (1994) *Mol. Cell. Biol.* 14, pp5898–5909.
Stump, W. T. & Hall, B. K. (1995) *RNA* 1, pp55–63.
Sutcliffe et al, (1978) *PNAS USA*, 75, p3737.
Witherell, G. W., Gott, J. M. & Uhlenbeck, 0. C. (1991) *Progress on Nucl. Acids Res. & Mol Biol.* 40, pp185–220.
Zlokamik et al, (1998) *Science*, 279, pp84–88.

What is claimed is:

1. A method for the identification of a compound that alters the affinity of interaction between an RNA-binding site and an RNA-binding compound, said method comprising the steps of:

a) expressing in a host cell
  i) a nucleic acid comprising a coding region for the RNA-binding compound,
  ii) a nucleic acid comprising a transcribed sequence comprising a coding region for a fluorescent marker protein, wherein the nucleic acid comprising the coding region for the fluorescent marker protein includes a binding site for the RNA-binding compound within a transcript transcribed from the transcribed sequence, wherein binding of the RNA-binding compound to the RNA-binding site represses translation of the transcribed sequence, b) contacting said host cell with a compound to be screened for altering the affinity of interaction between the RNA-binding site and the RNA-binding compound, and c) measuring the level of fluorescence in said host cells, wherein a compound that alters said level of fluorescence from the level that is seen in the absence of compound is indicative of a compound that alters the affinity of interaction between the RNA-binding site and the RNA-binding compound.

2. The method according to claim 1, wherein the RNA-binding compound is a protein.

3. The method according to claim 1, wherein the fluorescent marker protein is green fluorescent protein (GFP).

4. The method according to claim 1, wherein said host cell is a yeast cell.

5. The method according to claim 1, wherein said binding site for the RNA binding compound is in the 5' untranslated region of the nucleic acid coding for the fluorescent marker protein.

6. A method according to claim 1, wherein said nucleic acid coding for the fluorescent marker protein comprises a constitutive promoter that is operably linked to the coding sequence.

7. The method according to claim 1 wherein in step (c), a compound is identified that reduces the level of fluorescence in host cells from the level that is seen in the absence of the compound.

8. The method of claim 3, wherein the GFP is a GFP mutant that fluoresces at a different wavelength from that of wild type GFP.

9. The method of claim 8, wherein the mutation in the GFP mutant is Ser65Thr.

10. Amended) The method according to any one of claims 1–9, wherein said step of measuring the level of fluorescence in said host cells is performed using flow cytometry.

11. The method according to claim 10 wherein said said step of measuring the level of fluorescence in said host cells is performed using fluorescence-activated cell sorting (FACS).

* * * * *

SEQUENCE LISTING

<160> NUMBER OF SEQ ID NOS: 9

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Primer for
      Amplification by PCR

<400> SEQUENCE: 1
tttttaatta tgagcaaagg agaagaagaa cttttc                              36

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Primer for
      Amplification by PCR

<400> SEQUENCE: 2 tttttttctag attatttgta tagttcatcc atg                                33

<210> SEQ ID NO 3
<211> LENGTH: 73
<212> TYPE: DNA
<213> ORGANISM: Artificial Sequence
<220> FEATURE:
<223> OTHER INFORMATION: Description of Artificial Sequence: Green
      fluorescent protein indicator plasmid

<400> SEQUENCE: 3
aattatctac ttaagcttca acagtgcttg aacttaagaa cacaaaactc gagaacatat    60
ttttaatatt atg                                                       73

<210> SEQ ID NO 4
<211> LENGTH: 72
<212> TYPE: DNA
<213> ORGANISM: Artificial Sequence
<220> FEATURE:
<223> OTHER INFORMATION: Description of Artificial Sequence: Green
      fluorescent protein indicator plasmid

<400> SEQUENCE: 4
aattatctac ttaagcttca aagtgcttga acttaagaac acaaaactcg agaacatatt    60
tttaatatta tg                                                        72

<210> SEQ ID NO 5
<211> LENGTH: 70
<212> TYPE: DNA
<213> ORGANISM: Artificial Sequence
<220> FEATURE:
<223> OTHER INFORMATION: Description of Artificial Sequence: Green fluorescent protein indicator plasmid

<400> SEQUENCE: 5
aattatctac ttaagcgatt gcactcccgc ttaagaacac aaaactcgag aacatatttt    60
taatattatg                                                           70

<210> SEQ ID NO 6
<211> LENGTH: 70
<212> TYPE: DNA
<213> ORGANISM: Artificial Sequence
<220> FEATURE:
<223> OTHER INFORMATION: Description of Artificial Sequence: Green
      fluorescent protein indicator plasmid

<400> SEQUENCE: 6
aattatctac ttaagcgatt catctcccgc ttaagaacac aaaactcgag aacatatttt    60
taatattatg                                                           70

<210> SEQ ID NO 7
<211> LENGTH: 67
<212> TYPE: DNA
<213> ORGANISM: Artificial Sequence
<220> FEATURE:
<223> OTHER INFORMATION: Description of Artificial Sequence: Green
      fluorescent protein indicator plasmid

<400> SEQUENCE: 7
aattatctac ttaaggacca tcaggcctta agaacacaaa actcgagaac atatttttaa    60
tattatg                                                              67

<210> SEQ ID NO 8
<211> LENGTH: 67
<212> TYPE: DNA
<213> ORGANISM: Artificial Sequence
<220> FEATURE:
<223> OTHER INFORMATION: Description of Artificial Sequence: Green
      fluorescent protein indicator plasmid

<400> SEQUENCE: 8
aattatctac ttaaggacca taaggcctta agaacacaaa actcgagaac atatttttaa    60
tattatg                                                              67

<210> SEQ ID NO 9
<211> LENGTH: 66
<212> TYPE: DNA
<213> ORGANISM: Artificial Sequence
<220> FEATURE:
<223> OTHER INFORMATION: Description of Artificial Sequence: Green
      fluorescent protein indicator plasmid

<400> SEQUENCE: 9
aattatctac ttaaggacca taagccttaa gaacacaaaa ctcgagaaca tatttttaat    60
attatg                                                               66